US009126011B2

(12) United States Patent
Ash et al.

(10) Patent No.: US 9,126,011 B2
(45) Date of Patent: Sep. 8, 2015

(54) ANTI-CLOTTING INDWELLING CATHETER

(75) Inventors: Stephen R. Ash, Lafayette, IN (US);
Kenneth E. Brown, West Lafayette, IN (US); Roland K. Winger, West Lafayette, IN (US)

(73) Assignee: Merit Medical Systems, Inc., South Jordan, UT (US)

( * ) Notice: Subject to any disclaimer, the term of this patent is extended or adjusted under 35 U.S.C. 154(b) by 996 days.

(21) Appl. No.: 11/388,726

(22) Filed: Mar. 24, 2006

(65) Prior Publication Data

US 2007/0225682 A1    Sep. 27, 2007

(51) Int. Cl.
*A61M 25/00*    (2006.01)

(52) U.S. Cl.
CPC ......... *A61M 25/0074* (2013.01); *A61M 25/003* (2013.01); *A61M 25/0071* (2013.01); *A61M 25/0075* (2013.01); *A61M 25/0029* (2013.01); *A61M 25/0032* (2013.01); *A61M 25/0068* (2013.01); *A61M 25/0069* (2013.01); *A61M 25/0082* (2013.01); *A61M 2025/0031* (2013.01); *A61M 2025/0037* (2013.01); *A61M 2025/0076* (2013.01)

(58) Field of Classification Search
CPC ............. A61M 2025/0031; A61M 2025/0037; A61M 25/0074; A61M 25/0075; A61M 2025/0076; A61M 2025/0079
USPC ............. 604/164.01, 164.02, 164.08, 165.01, 604/165.02, 167.01, 284, 523, 533, 537, 604/538, 544, 93.01, 164.13, 264, 266, 528, 604/95.01, 95.04, 96.01
See application file for complete search history.

(56) References Cited

U.S. PATENT DOCUMENTS

| | | | |
|---|---|---|---|
| 396,754 A * | 1/1889 | Mayfield | 604/249 |
| 2,649,092 A | 8/1953 | Wallace | |
| 3,108,595 A | 10/1963 | Overment | |
| 3,397,699 A * | 8/1968 | Kohl | 604/105 |
| 3,841,308 A * | 10/1974 | Tate | 600/585 |
| 3,938,530 A | 2/1976 | Santomieri | |
| 4,256,102 A | 3/1981 | Monaco | |
| 4,327,722 A | 5/1982 | Groshong et al. | |
| 4,368,737 A | 1/1983 | Ash | |
| 4,549,879 A | 10/1985 | Groshong et al. | |
| 4,619,643 A | 10/1986 | Bai | |
| 4,657,536 A | 4/1987 | Dorman | |

(Continued)

FOREIGN PATENT DOCUMENTS

EP    0 348 136 A2    12/1989
EP    0 931 559 A2    7/1999

(Continued)

OTHER PUBLICATIONS

Supplementary European Search Report for PCT/US2007/015283 dated Jan. 20, 2011.

(Continued)

*Primary Examiner* — Kevin C Sirmons
*Assistant Examiner* — Shefali Patel
(74) *Attorney, Agent, or Firm* — Stoel Rives LLP

(57) ABSTRACT

A catheter for providing a blood flow includes a wall defining at least one lumen extending between a distal end and a proximal end. A distal end portion of the catheter is deformable to selectively open and close one or more ports in the wall to allow the blood flow into or out of the at least one lumen of the catheter.

16 Claims, 10 Drawing Sheets

(56) References Cited

U.S. PATENT DOCUMENTS

| | | | |
|---|---|---|---|
| 4,687,471 A | 8/1987 | Twardowski et al. |
| 4,701,166 A | 10/1987 | Groshong et al. |
| 4,772,268 A | 9/1988 | Bates |
| 4,822,345 A | 4/1989 | Danforth |
| 4,854,322 A | 8/1989 | Ash et al. |
| 4,895,561 A | 1/1990 | Mahurkar |
| 4,935,004 A | 6/1990 | Cruz |
| 4,973,319 A | 11/1990 | Melsky |
| 5,053,023 A | 10/1991 | Martin |
| 5,057,075 A | 10/1991 | Moncrief et al. |
| 5,156,592 A | 10/1992 | Martin et al. |
| 5,163,921 A | 11/1992 | Feiring |
| 5,209,723 A | 5/1993 | Twardowski et al. |
| 5,221,255 A | 6/1993 | Mahurkar et al. |
| 5,221,256 A | 6/1993 | Mahurkar |
| 5,250,034 A | 10/1993 | Appling et al. |
| 5,261,885 A | 11/1993 | Lui |
| 5,304,155 A | 4/1994 | Lui |
| 5,322,519 A | 6/1994 | Ash |
| 5,348,536 A | 9/1994 | Young et al. |
| 5,360,397 A | 11/1994 | Pinchuk |
| 5,374,245 A | 12/1994 | Mahurkar |
| 5,380,276 A | 1/1995 | Miller et al. |
| 5,395,353 A | 3/1995 | Scribner |
| 5,403,291 A | 4/1995 | Abrahamson |
| 5,405,320 A | 4/1995 | Twardowski et al. |
| 5,451,206 A | 9/1995 | Young |
| 5,470,585 A | 11/1995 | Gilchrist |
| 5,489,278 A | 2/1996 | Abrahamson |
| 5,509,897 A | 4/1996 | Twardowski et al. |
| 5,527,330 A | 6/1996 | Tovey |
| 5,533,980 A | 7/1996 | Sweeney et al. |
| 5,542,937 A | 8/1996 | Chee et al. |
| 5,569,182 A | 10/1996 | Twardowski et al. |
| 5,674,197 A | 10/1997 | Van Muiden et al. |
| 5,685,867 A | 11/1997 | Twardowski et al. |
| 5,702,365 A | 12/1997 | King |
| 5,733,248 A | 3/1998 | Adams et al. |
| 5,776,096 A | 7/1998 | Fields |
| 5,776,111 A | 7/1998 | Tesio |
| 5,807,311 A | 9/1998 | Palestrant |
| 5,807,339 A | 9/1998 | Bostrom et al. |
| 5,807,349 A | 9/1998 | Person et al. |
| 5,827,305 A * | 10/1998 | Gordon ................ 606/159 |
| 5,947,953 A | 9/1999 | Ash et al. |
| 5,961,486 A | 10/1999 | Twardowski et al. |
| 5,972,020 A * | 10/1999 | Carpentier et al. ........ 606/208 |
| 6,001,079 A | 12/1999 | Pourchez |
| 6,110,164 A | 8/2000 | Vidlund |
| 6,113,568 A | 9/2000 | Olaussen |
| 6,190,349 B1 | 2/2001 | Ash et al. |
| 6,270,489 B1 * | 8/2001 | Wise et al. ................ 604/508 |
| 6,315,757 B1 | 11/2001 | Chee et al. |
| 6,364,867 B2 | 4/2002 | Wise et al. |
| 6,409,699 B1 | 6/2002 | Ash |
| 6,482,169 B1 | 11/2002 | Kuhle |
| 6,547,761 B2 | 4/2003 | Liu |
| 6,569,150 B2 | 5/2003 | Teague et al. |
| 6,579,261 B1 | 6/2003 | Kawamura |
| 6,585,681 B2 | 7/2003 | Brugger et al. |
| 6,638,242 B2 | 10/2003 | Wilson et al. |
| 6,719,749 B1 | 4/2004 | Schweikert et al. |
| 6,749,580 B2 | 6/2004 | Work et al. |
| 6,814,718 B2 | 11/2004 | McGuckin, Jr. et al. |
| 6,858,019 B2 | 2/2005 | McGuckin, Jr. et al. |
| 6,872,198 B1 | 3/2005 | Wilson et al. |
| 6,911,014 B2 | 6/2005 | Wentling et al. |
| 6,916,313 B2 * | 7/2005 | Cunningham ............ 604/533 |
| 6,976,973 B1 | 12/2005 | Ruddell et al. |
| 6,997,894 B2 | 2/2006 | Caresio |
| 7,013,928 B2 | 3/2006 | Navis |
| 7,090,654 B2 | 8/2006 | Lotito et al. |
| 7,108,674 B2 | 9/2006 | Quinn |
| 7,141,035 B2 | 11/2006 | Haggstrom |
| RE39,451 E | 12/2006 | Kuhle |
| 7,182,746 B2 | 2/2007 | Haarala et al. |
| 7,322,953 B2 | 1/2008 | Redinger |
| 7,465,286 B2 | 12/2008 | Patterson et al. |
| 7,695,450 B1 | 4/2010 | Twardowski et al. |
| 7,776,005 B2 | 8/2010 | Haagstrom et al. |
| 7,799,014 B2 | 9/2010 | McGuckin, Jr. et al. |
| 7,922,687 B2 | 4/2011 | Gingles |
| 8,029,457 B2 | 10/2011 | Ash et al. |
| 8,052,659 B2 | 11/2011 | Ravenscroft et al. |
| 8,057,424 B2 | 11/2011 | Patterson et al. |
| 2001/0023333 A1 | 9/2001 | Wise et al. |
| 2002/0016584 A1 | 2/2002 | Wise et al. |
| 2002/0143292 A1 | 10/2002 | Flinchbaugh |
| 2003/0158538 A1 | 8/2003 | Deniega et al. |
| 2003/0191450 A1 | 10/2003 | Teague et al. |
| 2003/0204162 A1 | 10/2003 | Childers et al. |
| 2004/0087892 A1 | 5/2004 | Cunningham |
| 2004/0122418 A1 * | 6/2004 | Voorhees ................ 604/533 |
| 2004/0167463 A1 | 8/2004 | Zawacki et al. |
| 2004/0249337 A1 | 12/2004 | DiFore |
| 2005/0038413 A1 | 2/2005 | Sansoucy |
| 2005/0049555 A1 * | 3/2005 | Moorehead et al. ........ 604/122 |
| 2005/0096609 A1 | 5/2005 | Maginot et al. |
| 2005/0101941 A1 | 5/2005 | Hakky et al. |
| 2005/0177105 A1 | 8/2005 | Shalev |
| 2005/0245900 A1 | 11/2005 | Ash |
| 2005/0261663 A1 | 11/2005 | Patterson et al. |
| 2005/0277862 A1 | 12/2005 | Anand |
| 2006/0020256 A1 | 1/2006 | Bell et al. |
| 2006/0116629 A1 | 6/2006 | Tal et al. |
| 2006/0161118 A1 | 7/2006 | Maginot et al. |
| 2007/0225661 A1 | 9/2007 | Ash et al. |
| 2007/0225682 A1 | 9/2007 | Ash et al. |
| 2008/0009784 A1 * | 1/2008 | Leedle et al. .............. 604/43 |
| 2008/0082079 A1 | 4/2008 | Braga et al. |
| 2008/0082080 A1 | 4/2008 | Braga |
| 2008/0214980 A1 | 9/2008 | Anand |
| 2009/0024078 A1 | 1/2009 | Abe et al. |
| 2010/0081986 A1 | 4/2010 | Matson et al. |
| 2010/0204635 A1 | 8/2010 | Haarala et al. |
| 2010/0331780 A1 | 12/2010 | Bellisario et al. |
| 2011/0004197 A1 | 1/2011 | Sansoucy |
| 2011/0028904 A1 | 2/2011 | Watanabe et al. |
| 2011/0077577 A1 | 3/2011 | Sansoucy |
| 2011/0313401 A1 | 12/2011 | Ash et al. |

FOREIGN PATENT DOCUMENTS

| | | |
|---|---|---|
| WO | WO 94/09845 | 5/1994 |
| WO | WO 2005/025645 | 3/2005 |

OTHER PUBLICATIONS

Office Action dated May 30, 2008 for U.S. Appl. No. 11/528,733.
Office Action dated Nov. 4, 2008 for U.S. Appl. No. 11/528,733.
Office Action dated May 18, 2009 for U.S. Appl. No. 11/528,733.
Office Action dated Dec. 18, 2009 for U.S. Appl. No. 11/528,733.
Office Action dated May 21, 2010 for U.S. Appl. No. 11/528,733.
Office Action dated Dec. 21, 2010 for U.S. Appl. No. 11/528,733.
Notice of Allowance dated May 27, 2011 for U.S. Appl. No. 11/528,733.
Kohler et al., 'Central Venous Catheter Failure is Induced by Injury and can be Prevented by Stabilizing the Catheter Tip', Journal of Vascular Surgery, Jul. 1998.
Office Action dated Sep. 25, 2012 for U.S. Appl. No. 13/219,081.
International Search Report and Written Opinion dated Oct. 17, 2013 for PCT/US2013/050254.
Restriction Requirement dated Sep. 4, 2014 for U.S. Appl. No. 13/550,248.
Office Action dated Nov. 19, 2014 for U.S. Appl. No. 13/550,248.
Office Action dated Dec. 18, 2014 for U.S. Appl. No. 13/219,081.

* cited by examiner

ANTI-CLOTTING INDWELLING CATHETER

BACKGROUND

Patients with end stage renal disease (ESRD) must routinely receive dialysis treatments in order to live. Indwelling catheters are a useful dialysis access method for hemodialysis because they reduce the number of vein penetrations needed for repeated dialysis. Chronic central venous catheters for dialysis (CVCD) are the major long-term dialysis access for over 25% of ERSD patients or hemodialysis.

In a standard flow-through dialysis system, the CVCD must provide a first route for removal of blood and a second route for return of blood at a rate of at least 300 ml/min. A CVCD for a standard flow-through dialysis system can be formed by inserting two separate catheters into the jugular vein in a manner that forms a tunnel over the clavicle. In this arrangement, the catheter tips rest near the junction of the superior vena cava with the right atrium. The tip of the blood removal catheter, or arterial catheter, is placed 3-4 cm above the tip of the downstream blood return catheter, or venous catheter, in order to prevent mixture of cleansed blood with blood entering the arterial catheter.

As an alternative to the separate catheter for the standard flow-through dialysis system, a single-bodied catheter with two separate lumens can be used for dialysis access. In this arrangement, the tip of the arterial lumen is placed 3-4 cm above the tip of the venous lumen. Like the standard flow-through arrangement, this arrangement also prevents mixture of cleansed blood with blood entering the arterial lumen. As yet another alternative, dialysis can also be performed by using a single catheter with a single lumen. In this case, the dialysis machine delivers a quantity of untreated blood and then returns treated blood in alternating cycles.

Blood enters and exits the catheter lumen through ports or holes in the catheter. The design of these ports is highly variable, and similar concepts are employed in both single and dual lumen catheters. A first example is a catheter lumen having a single port at the tip for entrance or exit of blood. A second example is a catheter lumen having a blood exchange port located on the side of the lumen body toward its distal tip. Another example is a catheter lumen having multiple blood exchange ports axially placed around the side of the lumen body toward its distal tip. While all of the above CVCD designs work, there is room for improvement in the field, and there are problems with all current port designs for dialysis catheters.

Arterial catheter lumens that contain only one blood exchange port, no matter its location, run the risk of obstruction of the port by neighboring vein walls, by blood clotting in the exchange port, and by growth of a fibrin sheath around the distal end of the lumen and exchange port. Venous catheter lumens that contain only one blood exchange port, no matter its location, run the risk of obstruction by blood clotting in the exchange port and by growth of a fibrin sheath around the distal end of the lumen and the exchange port. Obstruction of the blood exchange port prevents the desired blood exchange rate of at least 300 ml/min from occurring. The degree of obstruction may render the indwelling catheter(s) ineffective for dialysis access. Therefore, when this level of obstruction occurs, the indwelling catheter(s) must be replaced.

Arterial catheter lumens containing multiple blood exchange ports around the distal end of the catheter reduce the occurrence of vein obstruction. However, the presence of multiple ports increases the risk of obstruction by blood clots because the multiple ports allow blood to flow into the lumen when idle, which can wash out the anticoagulant solution. The diminished presence of anticoagulant solution at the distal end of the catheter increases the amount of blood clotting in the ports and lumen. Obstruction of the blood exchange ports prevents the desired blood exchange rate of at least 300 ml/min from occurring. The degree of obstruction may render the indwelling catheter(s) ineffective for dialysis access. Therefore, when this level of obstruction occurs, the indwelling catheter(s) must be replaced.

Thus, there is a general need in the industry to provide methods and devices for the prevention of obstructions in the blood exchange ports of catheters and around the distal end of catheters. It is desired that these methods and devices prevent obstructions of the lumen due to clotting and fibrous sheath encasement of the tip of the catheter, as well as maintain the catheter anti-coagulant lock solution inside the lumen during idle periods between dialysis.

SUMMARY

The present invention is directed to an indwelling catheter. More particularly, but not exclusively, one aspect relates to an indwelling catheter adapted to prevent clotting and sheathing of the catheter's distal end. One application of the catheter includes non-exclusive use as a catheter for dialysis (CVCD). Other applications are also contemplated.

Another aspect relates to a catheter with a lumen for blood flow that includes a deformable wall portion to provide a path for blood flow in a first configuration and substantially closes the path when in a second configuration. Expansion of the walls of the catheter will also break loose any fibrous sheath beginning to form around the catheter tip A further aspect relates to a catheter with a lumen for blood flow that includes a wall portion that is deformed to open and close one or more ports in the wall portion by axially displacing a distal portion of the catheter including the one or more ports relative to a proximal portion of the catheter.

A further aspect relates to a catheter with a lumen for blood flow that includes a wall portion that is deformed to open and close one or more ports in the wall portion by radially deforming a distal portion of the catheter including the one or more ports.

A further aspect relates to a catheter with a lumen for blood flow that includes a wall portion that is deformed to open one or more ports in the wall portion by simultaneously axially and radially displacing a distal end of the catheter relative to a proximal portion of the catheter.

Yet another aspect relates to a catheter with a lumen for blood flow that includes a wall portion having a first shape to provide a port for blood flow and a second shape that substantially closes the port to prevent flow through the port.

Another aspect relates to a catheter with a lumen for blood flow that includes one or more ports that are opened by reducing a length of at least a portion of the catheter that includes the one or more ports.

A further aspect relates to a catheter that includes a self-closing port that retains a catheter lock solution in a lumen of the catheter when closed and permits blood flow through the passage when opened.

In another aspect, a catheter includes an elongate body defining a pair of lumens each for fluid flow therethrough. Each of the lumens extends between a distal and a proximal end and includes a port at the distal end thereof in communication with the lumen. The catheter also includes a pair of end caps at the distal ends of respective ones of the lumens and an actuating mechanism at the proximal ends of the lumens. Each of the end caps are coupled to the actuating mechanism with at least one actuating member extending in a wall along the respective lumen. The actuating mechanism is operable to independently and remotely move each of the end caps with the respective actuating member toward and away from the port of the respective lumen between closed and open conditions to permit fluid flow through the respective port.

In another aspect, a catheter includes an elongate body extending between a distal end and a proximal end. The body includes a wall defining at least one lumen for fluid flow therethrough and at least one port at the distal end of the elongate body in communication with the at least one lumen. The catheter also includes an end cap at the distal end and an actuating mechanism at the proximal end. The end cap is coupled to the actuating mechanism with at least one actuating member extending in the wall along the lumen. The actuating mechanism is operable to remotely move the end cap away from the port to an open condition and permit fluid flow through the port and the actuating mechanism is further operable to remotely move the end cap toward the distal end to a closed condition in sealing engagement with the body to prevent fluid flow through the port.

In a further aspect, a catheter includes a body defining at least one lumen extending along a longitudinal axis of the body. The body extends between a distal portion positionable in a vascular structure of a patient and a proximal end positionable outside the patient with the distal portion in the vascular structure. The distal portion of the body includes a plurality of adjacent wall segments extending therealong and located distally of the lumen. The wall segments together have a size and shape that substantially corresponds to a size and shape of the lumen transversely to the longitudinal axis. Adjacent ones of the wall segments define a port therebetween. Each of the ports includes a first closed condition formed by abutting engagement of the adjacent wall segments for preventing fluid flow between the lumen and the vascular structure through the ports. The ports include a second open condition formed by deforming at least one of the wall segments to open at least one of the ports to permit fluid flow between the vascular structure and the lumen through the ports.

Various means for opening and closing the catheter port are contemplated, including mechanical, pneumatic and hydraulic means. The closing means can be remotely actuated so that the port can remain indwelled in the patient while the port is opened and closed.

These and other aspects are further discussed below.

DESCRIPTION OF THE ILLUSTRATED EMBODIMENTS

Figure 2:
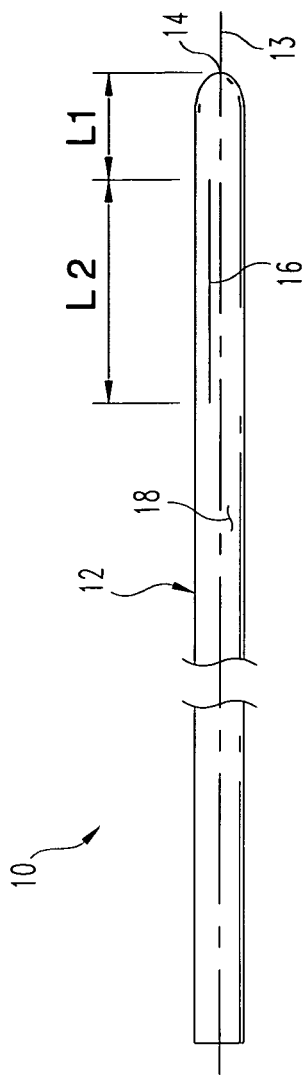
FIG. 2 is an elevation of the catheter of FIG. 1 with the ports in a closed condition.

For the purposes of promoting an understanding of the principles of the inventions, reference will now be made to the embodiments illustrated in the drawings and specific language will be used to describe the same. It will nevertheless be understood that no limitation of the scope of the inventions is thereby intended. Any alterations and further modifications of the principles of the inventions as illustrated or described herein are contemplated as would normally occur to one skilled in the art to which the inventions relate.

The present invention provides a catheter with at least one port adjacent a distal end of the catheter that can be selectively opened and closed. The at least one port can be open or closed while the at least one port is located in a vascular structure of a patient, such as a vein or artery. One application of the catheter contemplates that it is used in dialysis procedures, although other indwelling applications are also contemplated. The at least one port will be in the closed position between dialysis procedures to prevent blood from flowing through the port and to prevent clotting within the tip of the catheter. With the at least one port closed, the catheter can be injected with anticoagulant solution and the solution is retained within the catheter lumen.

It is contemplated that the at least one port allows fluid egress easier than fluid ingress when closed. Thus the concentration of anticoagulant within the lumen of the catheter can be maintained at the same level for many days or even weeks when the at least one port is closed. During dialysis, at least one port is opened by deforming the wall adjacent to the at least one port to allow ingress of blood through the port and into the lumen of the catheter. It is contemplated that opening the at least one port can lift the distal end of the catheter from the neighboring vessel surface, avoiding occlusion of the at least one port by a wall surface of the vessel structure. Further, opening of the at least one port can break loose any fibrous sheath that is forming around the distal end of the catheter adjacent the at least one port. Repeated opening and closing of the at least one port can provide a measure to prevent formation of a fibrous sheath around the distal end of the catheter.

The catheter can be made from any suitable bio-compatible material, including silicone, polyurethane, polyurethane-polycarbonate copolymer, or any other plastic or polymer material. The catheter can also include an antibacterial coating. The catheter can also be treated with an anti-infection agent, such as methylene blue, for example. The catheter can be of any suitable size for placement in a vessel structure, including sizes ranging from 8 to 15 French. Other sizes are also contemplated. The outer wall surface of the catheter can be cylindrical, D-shaped, double D-shaped, or split, for example. The catheter can also include a single lumen or multiple lumens.

Figure 3:
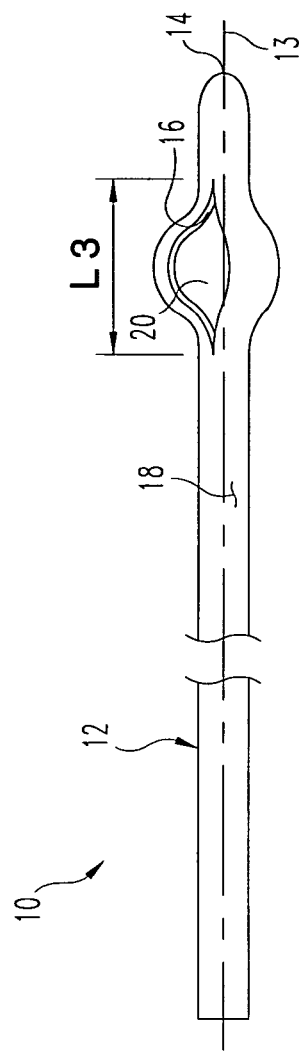
FIG. 3 is an elevation of the catheter of FIG. 1 with the ports in an opened condition
Figure 1:
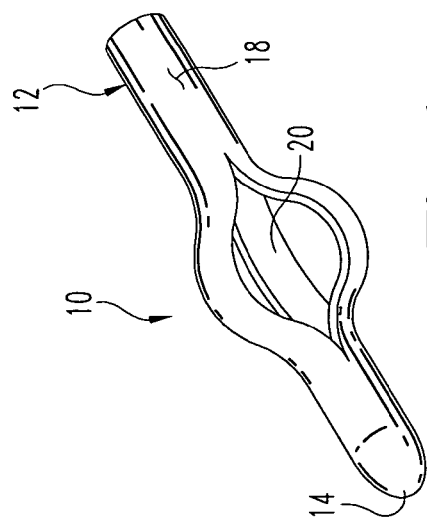
FIG. 1 is a perspective view of a distal portion of a catheter with open ports according to one embodiment of the invention.

Referring to FIGS. 1-3, there is shown a distal portion of a catheter 10 including a body 12 and a distal end 14. One or more ports 16 are provided adjacent distal end 14, and extend through wall 18 of body 12 in communication with a lumen 20. Distal end 14 can be closed with an integral tip or cap to prevent fluid flow therethrough. In the illustrated embodiment, each port 16 is an elongated slit or gill that extends generally parallel to the longitudinal axis 13 of body 12. Other embodiments contemplate other configurations for ports 16, including slits that extend transversely to the longitudinal axis 13 of body 12 and rounded openings with valve members that are opened and closed.

In FIGS. 1-3, three ports 16 are provided in wall 18 that extend along the longitudinal axis of body 12 and are spaced radially about body 12 approximately 120 degrees apart from one another. Other embodiments contemplate one more ports 16, including two ports, four ports, or five or more ports. It is further contemplated that the ports can be evenly spaced or unevenly spaced about body 12. In the illustrated embodiment each port 16 includes a distal end spaced a distance L1 from distal end 14, and extends along axis 13 for a length L2 to a proximal end of port 16. In one specific embodiment, length L1 is 5 millimeters and length L2 is 15 millimeters. It should be understood, however, that other distances for L1 and L2 are also contemplated, ranging from more than 0 millimeters to 20 or more millimeters.

Body 12 is comprised of a material with sufficient flexibility at least adjacent distal end 12 to facilitate manipulation of wall 18 to open and close ports 16. In FIG. 2, body 12 is in a first configuration or condition where ports 16 are closed. It is contemplated that in the closed condition wall 18 substantially seals ports 16 to prevent fluid flow from exiting or entering lumen 20 through ports 16 under a low pressure gradient. During injection of the catheter, enough pressure is generated to cause the lock solution to exit from the closed ports. In FIGS. 1 and 3, wall 18 has been manipulated to open one or more of the ports 16 to provide fluid communication between lumen 20 and an exterior of body 12.

Manipulation of wall 18 can include displacing or deforming adjacent portions of wall 18 along port 16. The deformed wall portions can provide a rounded or bulbous shape along ports 16. In one embodiment, ports 16 are opened by deforming wall 18 along ports 16 to reduce length L2 to length L3. One or more portions of wall 18 along ports 16 can be radially expanded or separated from an adjacent wall portion to open ports 16. The deformed portions of wall 18 can break loose any fibrous sheath formed thereabout. Furthermore, deformation of wall 18 can provide ports 16 with sufficient size to accommodate any required blood flow through lumen 20. When ports 16 are closed, portions of wall 18 along ports 16 abut one another along the entire length of each port 16 and with sufficient force to prevent fluid ingress and egress through wall 18 between lumen 20 and the vessel structure, and allow egress of fluid only under moderately positive pressure such as when filling the catheter with a lock solution.

It is further contemplated that an actuating assembly can be provided to facilitate opening and closing of ports 16, and maintain ports 16 in their opened and closed conditions. The actuating assembly can include an actuator adjacent a proximal end portion of catheter 10 so that the actuator is positioned outside the body of the patient and readily accessible by the surgeon. The actuating assembly can further include one or more actuating members coupled to the actuator and extending along the catheter to a location adjacent ports 16. The actuating members are movable or operable with the actuator to manipulate wall 18 and open or close ports 16 as desired.

Figure 4:
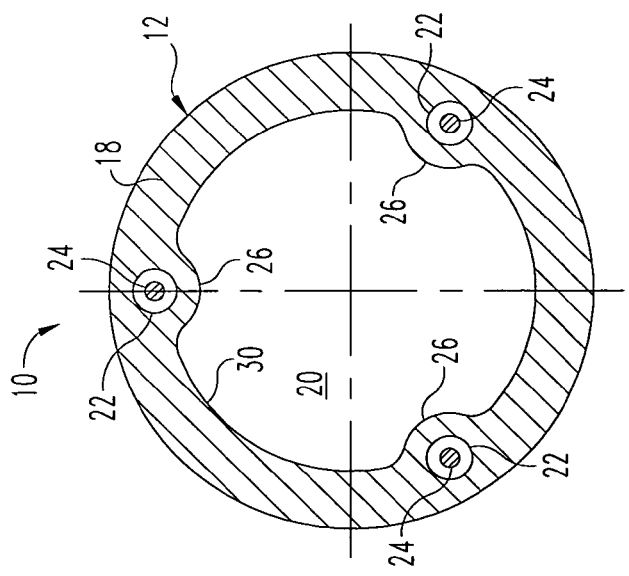
FIG. 4 is a sectional view through the body of the catheter of FIG. 1 taken transversely to its longitudinal axis.

In FIG. 4 there is shown a cross-section of body 12 taken transversely to longitudinal axis 13 to illustrate one embodiment of an actuating member 24. Wall 18 extends about lumen 20 and closes it from the exterior of body 12. A number of passages 22 are formed in wall 18 and each are sized to receive an actuating member 24 therethrough. Although three actuating members 24 are shown, it is also contemplated that one, two, or four or more actuating members 24 can be provided. Actuating members 24 extend from a distal end thereof adjacent distal end 14 of catheter 10 to a proximal end coupled to an actuator, as discussed further below.

In the illustrated embodiment, actuating members 24 extend through respective ones of enlarged portions 26 of wall 18. Enlarged portions 26 project into lumen 20 from inner surface 30 of wall 18, and provide a region of increased wall thickness to accommodate the insertion of the actuating members 24 in wall 18. Actuating members 24 can be in the form of a non-tubular wire, string, cable, tendon, rod, linkage, spring, or bar, for example. Actuating members 24 can be made from stainless steel, titanium, polymer, shape memory material, or other suitable material. Actuating members 24 can be coated with anti-bacterial agents and/or lubricious material to facilitate movement in wall 18. In other embodiments it is contemplated that one or more actuating members 24 can extend through lumen 20.

Actuating members 24 extend proximally from a location adjacent distal end 14 and are coupled with an actuator at their proximal ends. It is contemplated that the distal ends of actuating members 24 can be positioned proximally of ports 16, distally of ports 16, or along ports 16. The actuator is positioned along a proximal portion of catheter 10 and located outside the body of the patient so that the distal portion of catheter 10 can be remotely manipulated with the actuator mechanism to selectively open and close ports 16. In locations where actuating members 24 enter and/or exit the catheter body, the locations can be sealed and treated to prevent fluid leakage and infection.

Figure 5:
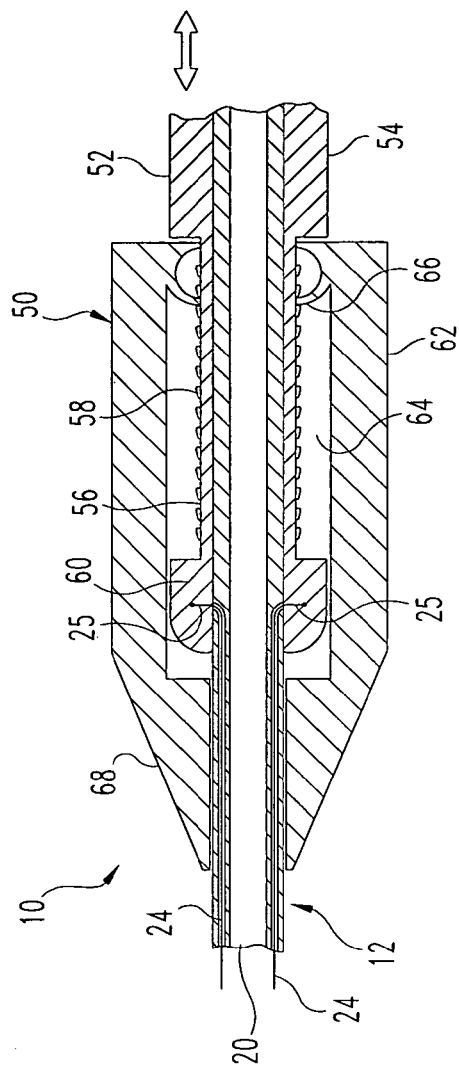
FIG. 5 is a longitudinal sectional view of one embodiment actuating mechanism for opening and closing the catheter of FIG. 1.

One embodiment of an actuator comprising an actuating mechanism with actuating members 24 is shown in FIG. 5 with a longitudinal cross-section through actuator 50. Actuator 50 is positioned about catheter body 12 and includes a hub 62 engageable with a slide-lock mechanism 52. Hub 62 includes a central passage 64 for receiving a portion of slide-lock mechanism 52 and catheter body 12. Hub 62 further includes a distal tapered portion 68, and is fixedly secured to catheter body 12. Slide lock mechanism 52 includes a proximal portion 54 which can be manually gripped or gripped with a tool to facilitate displacing slide-lock mechanism 50 axially relative to catheter body 12 and hub 62. Slide-lock mechanism 52 further includes a distal portion 56 extending into hub passage 64 and about catheter body 12. Distal portion 56 includes an engagement member 60 at a distal end thereof for engagement with proximal ends 25 of actuating members 24.

A number of locking surfaces 58 are formed along the length of distal portion 56 between locking member 66 and proximal portion 54. Hub 62 includes locking member 66 to engage locking surfaces 58 with sufficient force at any one of a number of positions along locking surfaces 58 and maintain slide-lock mechanism 52 at the corresponding position relative to hub 62. Locking member 66 is sufficiently resilient so that locking member 66 can be moved along locking surface 58 to adjust a positioning of slide-lock mechanism 52 relative to hub 62.

Wall 18 of catheter 10 can be manipulated by displacing slide-lock mechanism 52, and thus actuating members 24, proximally and axially relative to hub 60 and catheter body 12. The actuating members 24 pull on the portions of wall 18 adjacent ports 16 to open ports 16. Ports 16 can be closed by displacing slide-lock mechanism 52, and thus actuating members 24, distally and axially relative to hub 62 and catheter body 12. Locking member 66 engages slide-lock mechanism 52 to maintain ports 16 in either of the open and closed positions until sufficient force is applied to axially displace slide-lock mechanism 52 relative to hub 62. The actuating mechanism can further include one or more springs or other biasing members to facilitate maintaining ports 16 in either of the open or closed positions.

Figure 6:
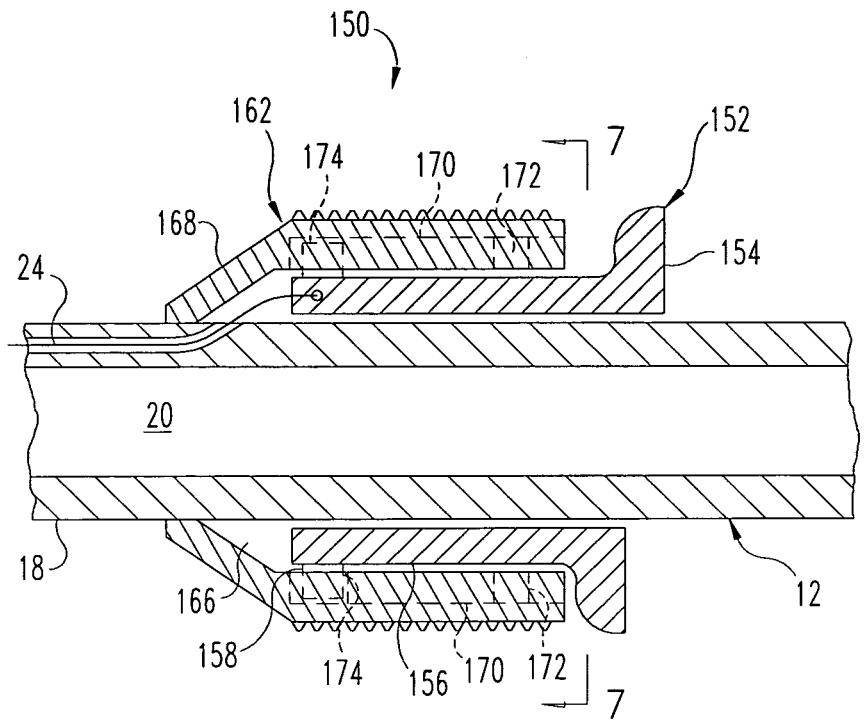
FIG. 6 is a longitudinal sectional view of another embodiment actuating mechanism.
Figure 7:
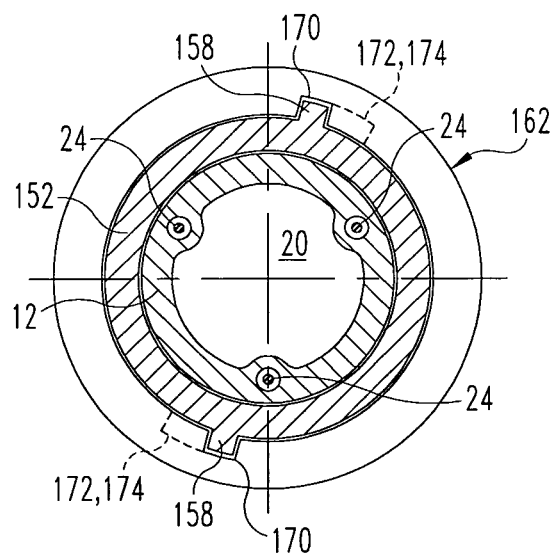
FIG. 7 is a sectional view through line 7-7 of FIG. 6.

Another embodiment of an actuator 150 useable with the actuating mechanism of catheter 10 is shown in FIGS. 6 and 7. Actuator 150 includes a hub 162 and a slide-lock mechanism 152. Slide lock mechanism 152 includes a proximal portion 154 for gripping by the user, and a distal portion 156 extending into passage 166 of hub 162. Actuating members 24 are secured to distal portion 156. Hub 162 includes locking surfaces formed by a pair of receptacles 170 formed therein in communication with passage 166. Locking members 158 extend from distal portion 156 and into corresponding ones of the receptacles 170. Receptacles 170 each include a proximal offset portion 172 and a distal offset portion 174.

To position and maintain ports 16 in a closed position, slide-lock mechanism 152 is distally advanced in hub 162 and rotated to position locking members 158 in distal offset portions 174. To position and maintain ports 16 in an open position, slide-lock mechanism 152 is proximally withdrawn from hub 162 and rotated to position locking members 158 in proximal offset portions 172. Positioning of the locking members 158 in the offset portions prevents axial movement of slide-lock mechanism 152 relative to hub 162. It is also contemplated that offset portions for receptacle 170 can be provided between proximal and distal offset portions 172, 174 to provide for variability in the degree of opening of ports 16 and for changes in the physical properties of catheter body 12 and actuating members 24 over time.

Figure 8:
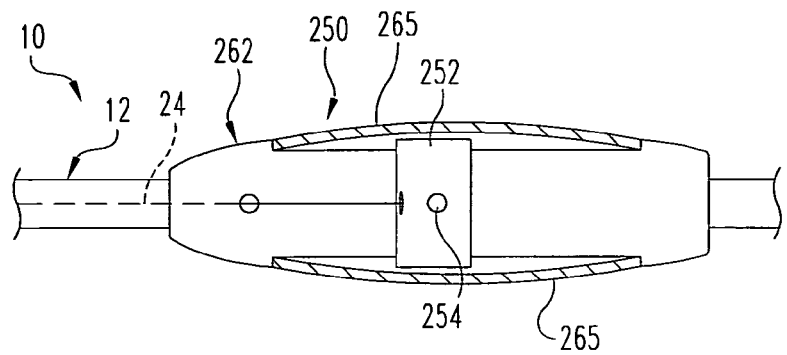
FIG. 8 is a longitudinal elevation view in partial section view of another embodiment actuating mechanism.
Figure 9:
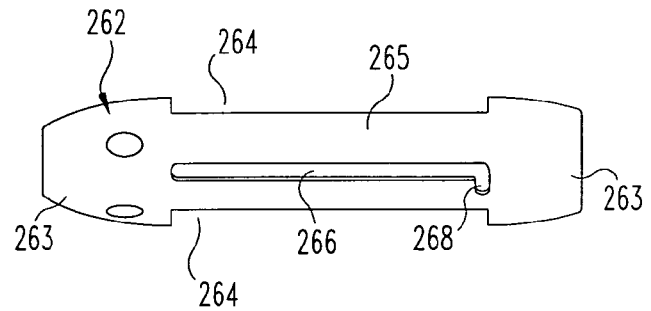
FIG. 9 is an elevation view of a hub member comprising a portion of the actuating mechanism of FIG. 8.

Another embodiment of an actuator 250 for an actuating mechanism for catheter 10 is shown in FIGS. 8 and 9. Actuator 250 includes a hub 262 and a slide-lock mechanism 252. Slide lock mechanism 252 includes one or more locking members 254 extending therefrom. Actuating members 24 are secured to slide-lock mechanism 252 and movable therewith. Hub 262 includes a pair of opposite end portions 263 engageable to catheter body 12. Hub 262 further includes a pair of opposite slotted ports 264 and a pair of opposite sidewalls 265 extending between the opposite slotted ports 264. At least one receptacle 266 extends through at least one of the sidewalls 265. Receptacle 266 includes an offset portion 268 at a proximal end thereof.

Slide-lock mechanism 252 is positioned between sidewalls 265 and moveable therebetween axially along catheter body 12. Locking member 254 extends into receptacle 266, and is movable therealong with movement of slide-lock mechanism 252 for positioning into offset portion 268 to secure ports 16 in an open condition. A second distal offset receptacle portion (not shown) can be provided to secure ports 16 in a closed condition, and offset portions can be provided along the length of receptacle 266 to accommodate variation in opening of ports 16 and the physical properties of catheter body 12 and actuating members 24.

Figure 10:
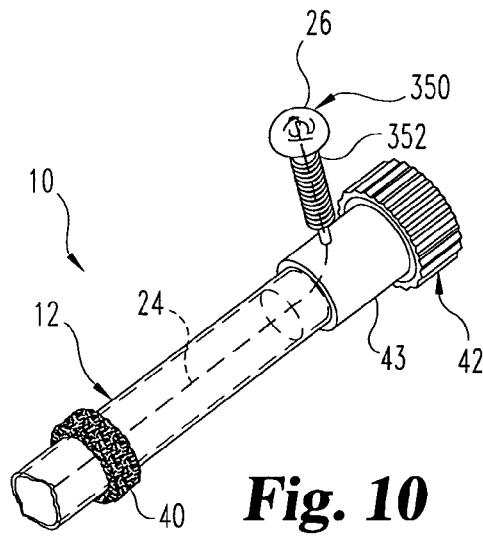
FIG. 10 is a perspective view of another embodiment actuating mechanism and its position when the ports are in a closed condition.
Figure 11:
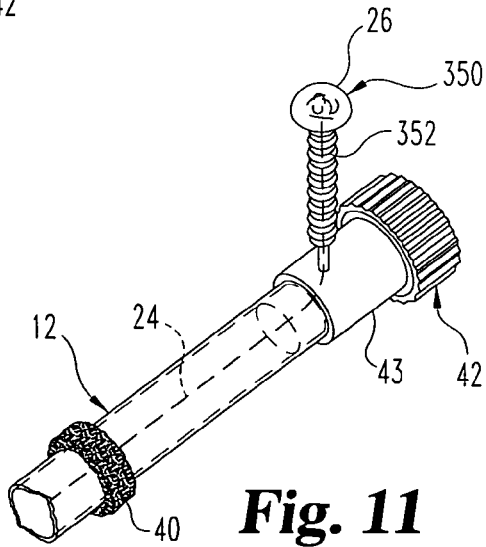
FIG. 11 is a perspective view of the actuating mechanism of FIG. 10 and its position with the ports in an open condition.

Another embodiment actuator 350 is shown in FIGS. 10 and 11. In FIGS. 10 and 11 the proximal end of catheter 10 is shown with a cuff 40 positionable below the skin level to assist in maintaining the catheter in the patient and prevent leakage around catheter 10. The proximal end of catheter 10 further includes a luer lock fitting 42. Actuator 350 includes a tube member 352 through which actuating member 24 extends. Tube member 352 extends transversely from a side of a distal portion 43 of fitting 42. The portion of tube member 352 nearest to hub 43 includes a plastic material, such as silicone glue, therein to serve as a seal around the actuating member 24. Actuating member 24 extends through tube member 352 and the plastic material to an enlarged end member 26 at the proximal end of actuating member 24. End member 26 is attached to tube member 352 and assures that actuating member 24 moves with the expansion and compression of tube member 352. Tube member 352 includes an accordion-like shape along its length with a wall that folds upon itself to allow expansion and contraction of the length of tube member 352. Tube member 352 can be glued or sealed at each end to prevent contamination.

Figure 12:
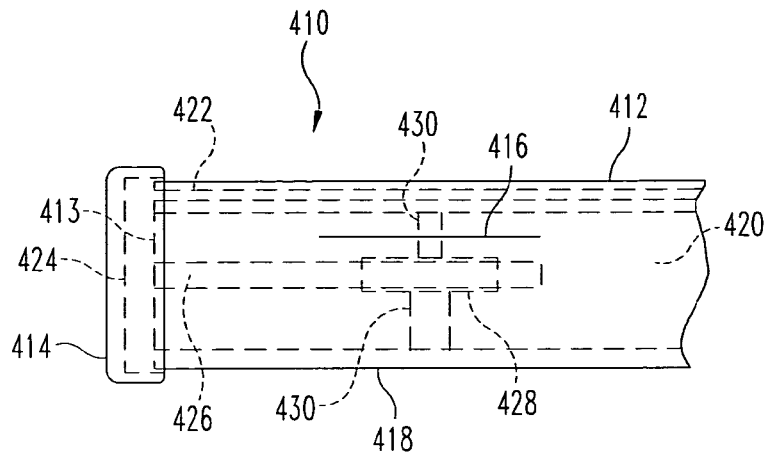
FIG. 12 is an elevation view of a distal portion of another embodiment catheter with its ports in a closed condition.
Figure 13:
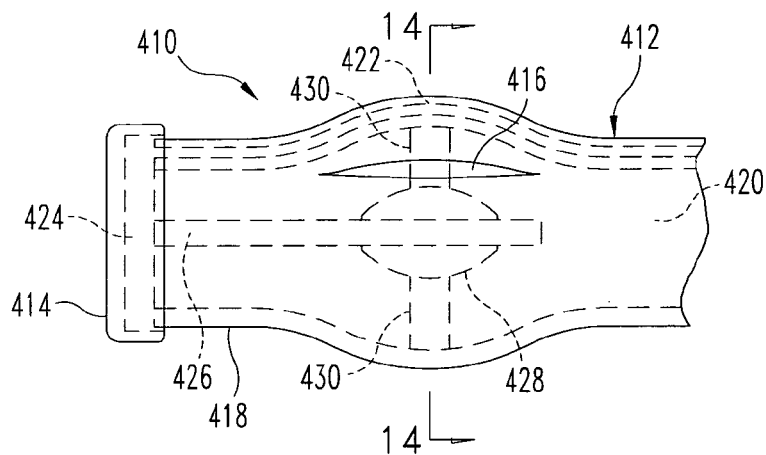
FIG. 13 is an elevation view of the catheter of FIG. 12 with its ports in an opened condition.
Figure 14:
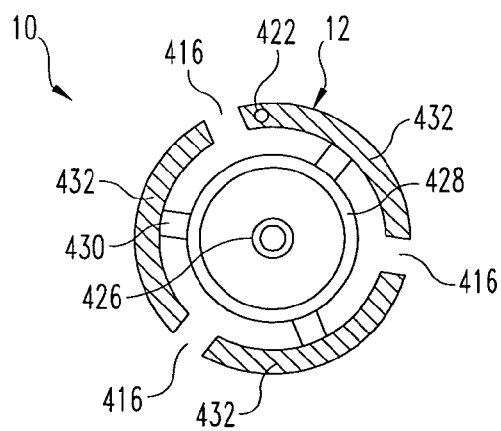
FIG. 14 is a sectional view through line 14-14 of FIG. 13.

FIGS. 12-14 illustrate various views of a distal portion of a catheter according to another embodiment. Catheter 410 includes a catheter body 412 with a central lumen 420. The distal end 413 of body 412 is sealed with a cap 414, which may be integral with body 412 or a separate member sealingly engaged thereto. Body 412 includes a wall 418 extending about lumen 420. Wall 418 includes one or more ports 416, which can be elongated slits or gills as discussed above with respect to catheter 10.

Wall 418 further includes an inflation lumen 422 formed therein for delivery of a fluid, such as saline, air, gas, or other suitable fluid, to inflate an enlargement member 428. Enlargement member 428 is positioned in lumen 420, and is shown in a reduced-size configuration in FIG. 12 and an enlarged configuration in FIGS. 13 and 14. Enlargement member 428 can be in the form of a balloon, bag, bladder, diaphragm or other device capable of opening and closing ports 416 as it is enlarged and reduced.

End cap 414 and distal end 413 define a pocket 424 therebetween. Inflation lumen 422 is in fluid communication with pocket 424 to deliver fluid thereto. An inflation tube or stem 426 extends through lumen 420 from distal end 413. Stem 426 includes an internal passage in fluid communication with pocket 424 and enlargement member 428. Accordingly, fluid can be moved through inflation lumen 422 to pocket 424 and through stem 426 to enlargement member 428 to selectively enlarge and reduce enlargement member 428.

One or more arms 430 extend between enlargement member 428 and an inner surface 419 of wall 418 at wall portions 432 adjacent ports 416. As shown in FIG. 14, an arm 430 is provided between each port 416. As enlargement member 428 is enlarged, arms 430 push outwardly to radially deform wall portions 432 of wall 418 and effecting separation of the adjacent wall portions 432 and opening each port 416. In the illustrated embodiment, there are provided three arms 430, three ports 416, and three wall portions 432 between adjacent ones of the ports 416.

Arms 430 space wall portions 432 from the enlarged enlargement member 428 to provide a path for blood flow through the open ports 416 and about the enlarged enlargement member 428 into lumen 420. When the fluid is removed from enlargement member 428, its size reduces and arms 430 pull wall portions 432 into alignment with catheter body 412, closing ports 416 to prevent flow therethrough. To effect a positive force between adjacent sides of wall portions 432 to sealingly close ports 416, a negative pressure can be imparted to enlargement member 428, drawing wall portions 432 radially inwardly in contact with one another.

Other configurations for ports 416 are also contemplated, including a single port 416 with a pair of wall portions 432 positioned adjacent to the sides thereof. In another embodiment, a pair of ports 416 are provided at opposite sides of body 412, and a pair of wall portions 432 are centrally spaced between the opposite ports 416. In a further embodiment, four or more ports 416 with a corresponding number of wall portions positioned between adjacent ports are contemplated. Any one or all of the wall portions of the embodiments may be provided with an arm extending between the wall portion and the enlargement member.

Other configurations are also contemplated for delivering fluid to enlarge enlargement member 428 are contemplated. For example, one or more of the arms 430 can include a passage to deliver fluid to enlargement member 428. In another embodiment, enlargement member 428 is in direct fluid communication with enlargement lumen 422.

The catheter embodiment in FIGS. 12-14 utilizes pneumatic or hydraulic means to manipulate wall 418 of catheter 410 to selectively open and close ports 416. When ports 416 are closed, blood flow is prevented from entering lumen 420 and a lock solution can be retained in lumen 420 to prevent coagulation.

Other variations for stem 426 and arms 430 are also contemplated. For example, stem 426 can include a bellows, accordion-like, or other suitable configuration that is axially expandable and compressible, or otherwise axially movable, to reposition stem 426 in lumen 420. Arms 430 can include a wire form or other structure pivotally connected to stem 426 and wall portions 432. When stem 426 is in a first axial configuration and positioning relative to wall portions 432, the arms 430 are angled between stem 426 and wall portions 432 to maintain ports 416 in a closed condition. When stem 426 is moved to a second axial configuration, the ends of arms 430 connected to stem 426 move therewith, and as the arms become more orthogonally oriented to stem 426, the arms 430 push radially outwardly on wall portions 432 to open ports 416.

In still another embodiment arms 430 expand along their axes between stem 426 and wall portions 432 to move wall portions 432 away from one another to open ports 416. Arms 430 are collapsible along their axes to move wall portions 432 toward one another and close ports 416. In this embodiment, stem 426 can be non-expandable and/or non-movable. In one form, arms 430 include an accordion or bellows-like configuration along their length. In another form, arms 430 include a balloon-like configuration and are at least axially expandable, and can also be radially expandable.

Figure 15:
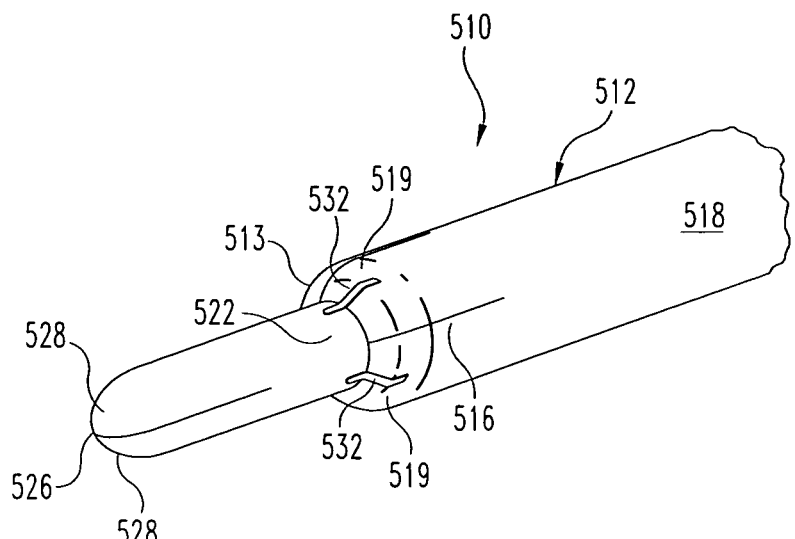
FIG. 15 is a perspective view of a distal portion of another embodiment catheter with its ports in a closed condition.
Figure 16:
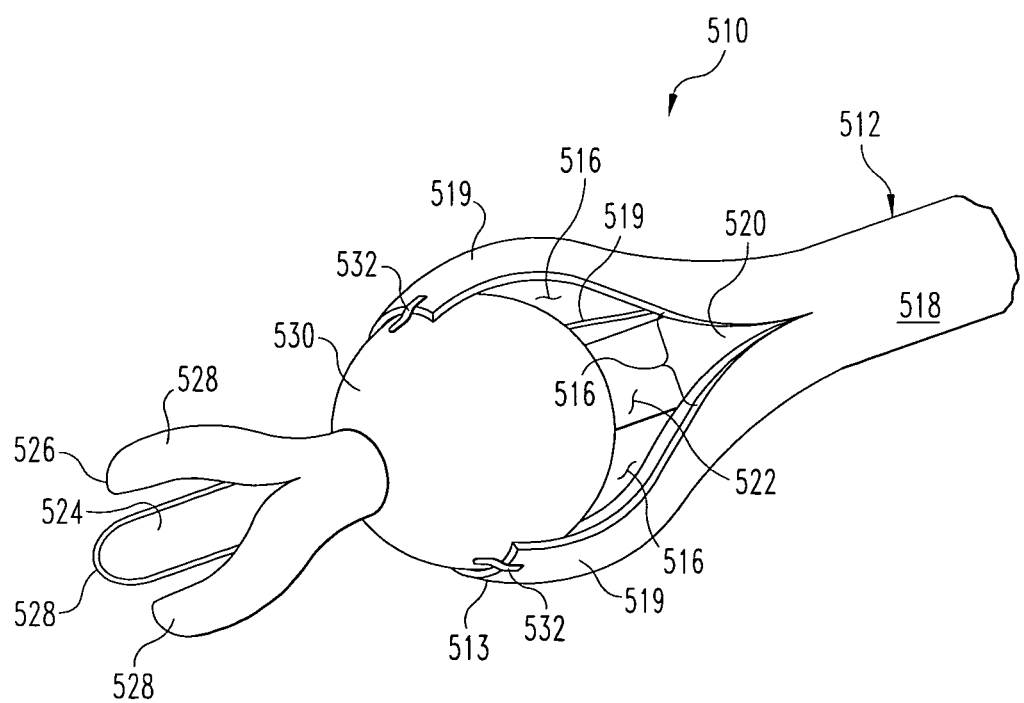
FIG. 16 is the distal portion of the catheter of FIG. 15 with its ports in an open position.

FIGS. 15 and 16 show a distal portion of another embodiment catheter. In FIG. 15 the distal ports of the catheter are in a closed condition, and in FIG. 16 the distal ports are in an open condition. Catheter 510 includes a catheter body 512 with a central lumen 520 defined by a first wall 518. The distal end 513 of first wall 518 is openable to allow fluid to flow therethrough, and closeable to prevent fluid flow therethrough. First wall 518 includes one or more ports 516, which can be elongated slits or gills that extend to distal end 513. Adjacent ones of the ports 516 are separated by wall portions 519 extending therebetween.

A second wall 522 extends through lumen 520 and forms a second lumen 524. Second lumen 524 opens at distal end 526 of second wall 522. Second wall 522 includes a number of end members 528 that are normally biased to the closed position to prevent fluid flow from entering second lumen 524. Pressure from fluid in second lumen 524 causes end members 528 to move away from one another and separate, allowing fluid egress from lumen 524 through distal end 526. Other embodiments contemplate that lumen 524 is not used for blood flow. Still other embodiments contemplate that catheter 510 is provided without a lumen 524.

Second wall 522 further includes an enlargement member 530 formed therearound proximally of end members 528. Enlargement member 530 is received in lumen 520, and has a collapsed or reduced-size configuration, as shown in FIG. 15, and an enlarged or expanded configuration, as shown in FIG. 16. Second wall 522 can include an inflation lumen (not shown) in fluid communication with an interior of enlargement member 530 for delivery and removal of fluid from enlargement member 530. The fluid can be saline, air, gas, or other suitable fluid, to inflate or enlarge enlargement member 530.

Enlargement member 530 can be in the form of a balloon, bag, bladder, diaphragm or other device capable of opening and closing ports 516 as it is enlarged or reduced. When in the unexpanded condition of FIG. 15, adjacent ones of the wall portions 519 abut one another so that ports 516 are closed. Fluid flowing in second lumen 524 may exit lumen 524 through the distal end opening of second wall 522 provided the fluid pressure is sufficient to open distal end 526 by separating end members 528. If fluid ingress into lumen 520 is desired, fluid can be delivered to enlargement member 530 to cause it to enlarge or expand. As it expands, it acts on wall portions 519 to radially deform wall 518 and cause ports 516 to open as wall portion 519 separate.

Arms 532 can be provided between enlargement member 530 and wall portions 519 to facilitate radial deformation of wall 518, assure active closing of ports 516, and prevent detachment of wall portions 518 from enlargement member 530. Arms 532 attach wall portions 519 to enlargement member 530. In one embodiment, there is zero clearance between enlargement member 530 and wall portions 519, and fluid flow is directed through open ports 516 proximally of distal end 513. Arms 532 are provided with sufficient elasticity to span the differing radii of curvature between the distal ends of wall portions 519 and the enlarged enlargement member 530. In another embodiment, arms 532 maintain separation between the inner surface of wall 518 and enlargement member 530, facilitating fluid flow through the distal end opening of first wall 518 and also through the ports 516 between the adjacent wall portions 519.

In the illustrated embodiment, arms 532 extend distally of the respective wall portions 519 and into contact with enlargement member 530. It is also contemplated that one or more of the arms 532 can also be located within lumen 520, and can include any configuration as discussed above with respect to arms 430. In the illustrated embodiment, there are provided three arms 532, three ports 516, and three wall portions 519 between adjacent ones of the ports 516.

Wall portions 519 may or may not be spaced from the enlarged enlargement member 530. When enlargement member 530 is enlarged, the open ports 516 provide a path for blood flow therethrough and about the enlarged enlargement member 530 into lumen 520. When the fluid is removed from enlargement member 530, its size reduces and wall portions 519 collapse into alignment and abutting engagement with one another, closing ports 516 to prevent flow therethrough. In one embodiment, arms 532 can be engaged to enlargement member 530 and wall portions 519 to pull wall portions 519 to the closed condition. Arms 532 can assure a positive closure of ports 516 when enlargement member 530 is in its reduced size configuration. In another embodiment, wall portions 519 are naturally biased via a living hinge connection with wall 518 toward the closed condition.

In a further embodiment, arms 532 can be secured to the distal ends of wall portion 519 at one end of each of the arms 532 and include an opposite end that rides or floats along enlargement member 530 as it is expanded and collapsed. In still another embodiment, arms 532 can expand along their axes between enlargement member 530 and wall portions 519 to move wall portions 519 away from one another to open ports 516 as fluid is delivered to arms 532. Arms 532 can be collapsible along their axes to move wall portions 519 toward one another and close ports 516. In this embodiment, enlargement portion 530 can be non-expandable or non-enlargeable. In one form, arms 532 include an accordion or bellows-like configuration along their length. In another form, arms 532 include a balloon-like configuration and are at least axially expandable, and can also be radially expandable.

Other configurations for ports 516 are also contemplated, including a single port 516 with a pair of wall portions 519 positioned adjacent to the sides thereof. In another embodiment, a pair of ports 516 is provided at opposite sides of body 512, and a pair of wall portions 519 are centrally spaced between the opposite ports 516. In a further embodiment, four or more ports 516 with a corresponding number of wall portions are positioned between adjacent ports are contemplated. For any of the embodiments, one or more arms 532 may be provided between the enlargement member and one or more the wall portions, or no arms 532 are provided.

The catheter embodiment in FIGS. 15-16 utilizes pneumatic or hydraulic means to manipulate wall 518 of catheter 510 to selectively open and close ports 516. When ports 516 are closed, blood flow is prevented from entering lumen 520 and a lock solution can be retained in lumen 520 to prevent coagulation. Lock solution can also be maintained in lumen 524 to prevent coagulation.

Figure 17:
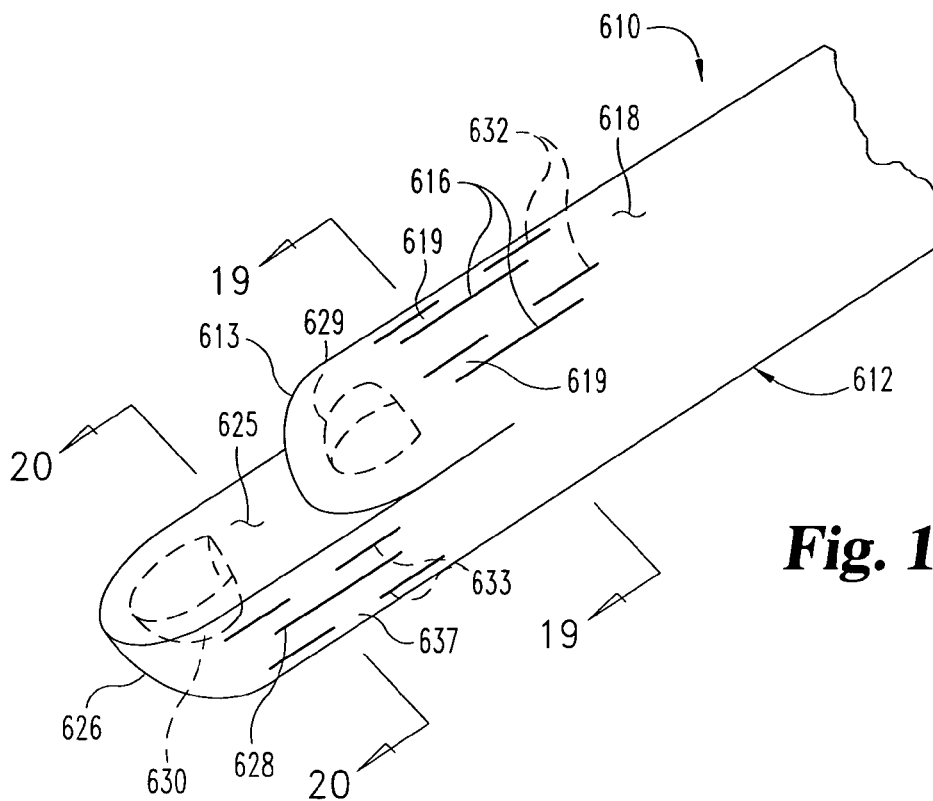
FIG. 17 is a perspective view of a distal portion of another embodiment catheter with its ports in a closed condition.

FIGS. 17-21 show a distal portion of another embodiment catheter 610. In FIG. 17 the distal ports of catheter 610 are in a closed condition, and in FIG. 18 the distal ports are in an open condition. Catheter 610 includes a catheter body 612 with a first lumen 620 defined by a first wall 618. The distal end 613 of first wall 618 is closed, and one or more ports 616 are formed in first wall 618 in communication with first lumen 620. Adjacent ones of the ports 616 are separated by first wall portions 619 extending therebetween. Ports 616 are openable by deforming wall portions 619 to allow fluid to flow therethrough, and are closeable to prevent fluid ingress or egress from lumen 620. The one or more ports 616 can be elongated slits or gills that extend along first wall 618 to a location proximal of distal end 613.

Body 612 also includes a second wall 622 extending about a second lumen 624. Second lumen 624 is closed at distal end 626 of second wall 622. Second wall 622 includes a number of ports 628 separated by wall portions 637 therebetween. Ports 628 are normally biased to the closed position to prevent fluid flow therethrough. Pressure from fluid in second lumen 624 causes wall portions 637 to move away from one another and separate to open ports 628 allowing fluid ingress and egress from lumen 624 through ports 628.

A common wall portion 625 extends between and separates lumens 620, 624. In the illustrated embodiments, first and second walls 618, 622 form D-shaped lumens 620, 624. Other embodiments contemplate other shapes for lumens 620, 624, including circular, oval, polygonal, and irregular shapes, for example. Other embodiments contemplate no common wall portion between lumens 620, 624. Rather, each of the lumens is circumscribed by a separate wall. The separate walls can be separate or split from one another at least along the distal portion of catheter 610. In another form, the walls can be engaged to one another yet are splittable to allow the walls to be separated from one another if desired.

Figure 18:
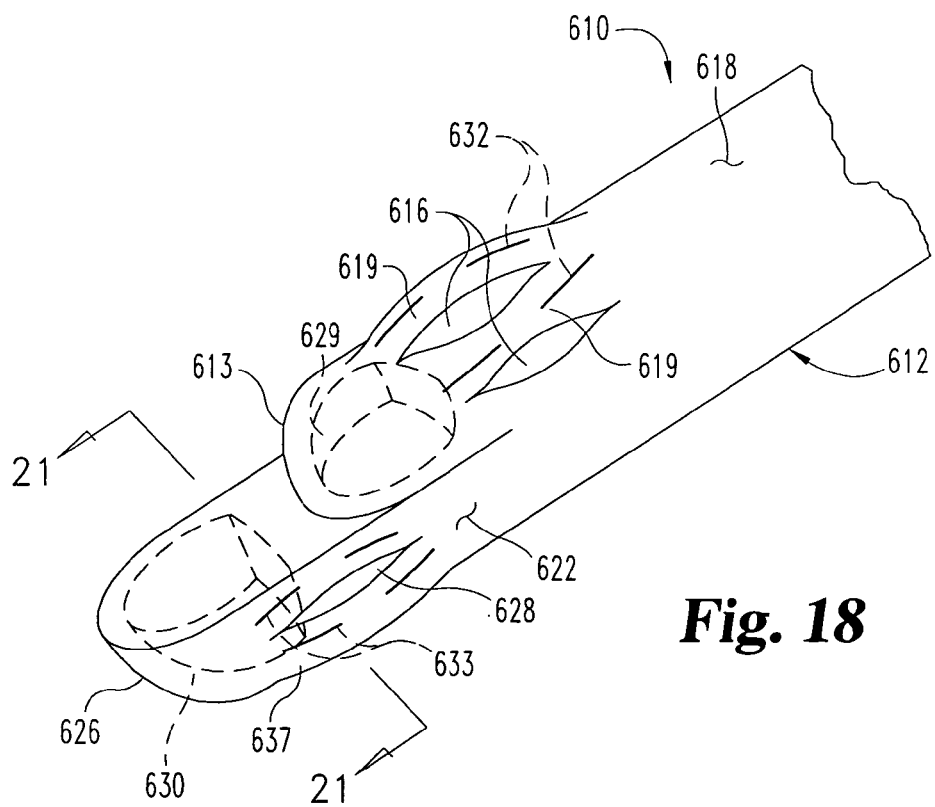
FIG. 18 is the distal portion of the catheter of FIG. 17 with its ports in an open position.
Figure 19:
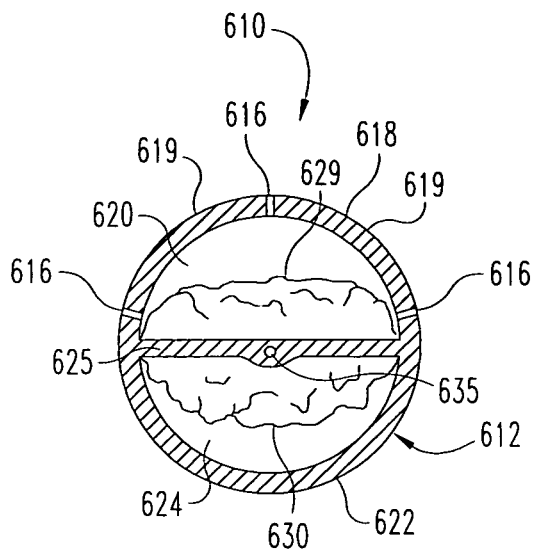
FIG. 19 is a section view along line 19-19 of FIG. 17.
Figure 20:
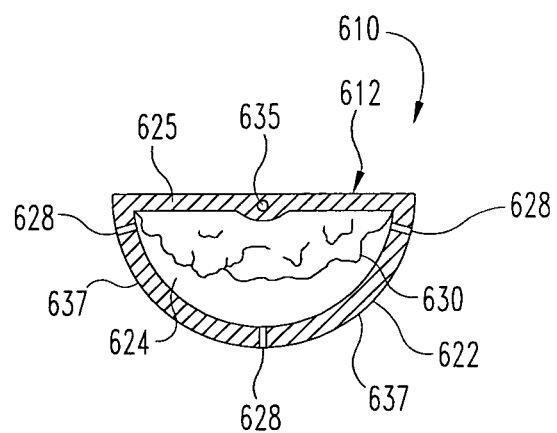
FIG. 20 is a section view along line 20-20 of FIG. 17.
Figure 21:
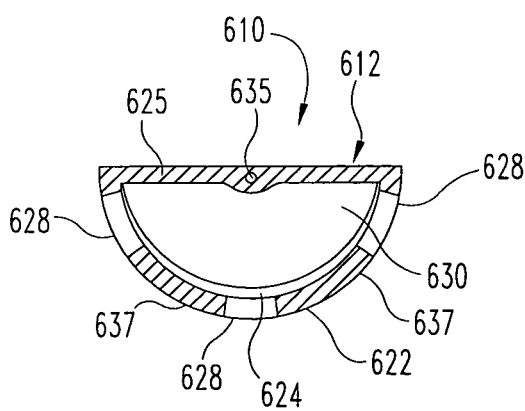
FIG. 21 is a section view along line 21-21 of FIG. 18.

First wall 618 includes a first enlargement member 629, and second wall 622 includes a second enlargement member 630. Enlargement members 629, 630 can be received in respective ones of the lumens 620, 624 and have a collapsed or reduced-size configuration, as shown in FIG. 17, and an enlarged or expanded configuration, as shown in FIG. 18. At least one of the first and second walls 618, 622 or common wall 625 can include an inflation lumen 635 in fluid communication with an interior of enlargement members 629, 630 for delivery and removal of fluid from enlargement members 629, 630. The fluid can be saline, air, gas, or other suitable fluid, to inflate or enlarge enlargement members 629, 630.

Inflation lumen 635 can be provided in communication with the interiors of one or more of the enlargement members 629, 630 to provide a path for fluid delivery thereto and removal therefrom to selectively enlarge and reduce the size of enlargement members 629, 630. Inflation lumen 635 can extend between and communicate with each of the interiors of enlargement members 629, 630 so that enlargement members 629, 630 can be simultaneously enlarged or simultaneously reduced in size. Other embodiments contemplate a separate inflation lumen in communication with respective ones of the enlargement members 629, 630. Inflation lumen 635 is shown in common wall 625. Other embodiments contemplate one or more inflation lumens in first wall 618 and/or second wall 622.

Enlargement members 629, 630 can be in the form of a balloon, bag, bladder, diaphragm or other device capable of opening and closing ports 616, 628 as it is enlarged or reduced. When in the unexpanded condition of FIG. 17, adjacent ones of the wall portions 619, 637 abut one another so that ports 616, 628 are closed. Fluid can be delivered to enlargement member 629 to cause it to enlarge or expand. As it expands, it acts on wall portions 619 to radially deform first wall 618 and cause ports 616 to open as wall portions 619 separate. Similarly, fluid can be delivered to enlargement member 630 to cause it to enlarge or expand. As it expands, it acts on wall portions 637 to radially deform second wall 622 and cause ports 628 to open as wall portions 637 separate from one another. Pneumatic or hydraulic means can be used to manipulate the enlargement members 629, 630 to selectively open and close ports 616, 628. When ports 616, 628 are closed, blood flow is prevented from entering lumens 620, 624 and a lock solution can be retained in lumens 620, 624 to prevent coagulation.

One method for fabricating catheter 610 contemplates forming body 612 so that the distal ends of lumens 620, 624 are initially open. Enlargement members 629, 630 are inserted in a collapsed condition through respective ones of the distal end openings. A plug is then positioned in each of the distal end openings. The material of the plug and catheter body is then re-flowed or otherwise sealed to seal the enlargement members in the respective lumens. A pin or other hole forming device is inserted through the wall or walls to form a passage between the interior of the enlargement member and the one or more inflation lumens. The hole is then capped or sealed to seal the enlargement lumen and the enlargement members.

Arms 632, 633 can be provided in wall portions 619, 637 along the respective ports 616, 628. Arms 632, 633 can include shape recovery properties to facilitate closing of ports 616, 628 after releasing the deformation force on walls portions 619, 637. Arms 632, 633 can be embedded in the wall portions 619, 637, and have the form of a wire or other bendable member that moves with the wall portion 619, 637 when deformed to open the ports. The shape recovery properties of the arms 632, 633 maintain the ports 616, 628 in a positively closed condition to allow containment of lock solution or other fluid in lumens 620, 624. Various forms for arms 632, 633 are contemplated, including spring steel, nitinol, or other suitable material. Other embodiments contemplate that wall portions 619, 637 are made from material with shape recovery properties to effect positive closure of the ports.

When enlargement members 629, 630 are enlarged, the open ports 616, 628 provide a path for blood flow therethrough and about the enlarged enlargement members 629, 630. When the fluid is removed from enlargement members 629, 630 their size reduces and wall portions 619, 637 collapse into alignment and abutting engagement with one another, closing ports 616, 628 to prevent flow therethrough. Arms 632, 633 can assure a positive closure of ports 616, 628 when enlargement members 629, 630 are in a reduced size configuration. In another embodiment, wall portions 619, 637 are naturally biased to the closed position via a living hinge connection with walls 618, 622 or by material properties of wall portions 619, 637.

Other configurations for ports 616, 628 are also contemplated, including a single port between a pair of adjacent wall portions. In another embodiment, a pair of ports is provided at opposite sides of the respective wall portions. In a further embodiment, four or more ports are provided in the respective wall portions with a corresponding number of wall portions between adjacent ports. For any of the embodiments, the wall portions may the same number of ports, or may have a differing number of ports. Ports may also extend non-longitudinally in the respective walls.

Figure 22:
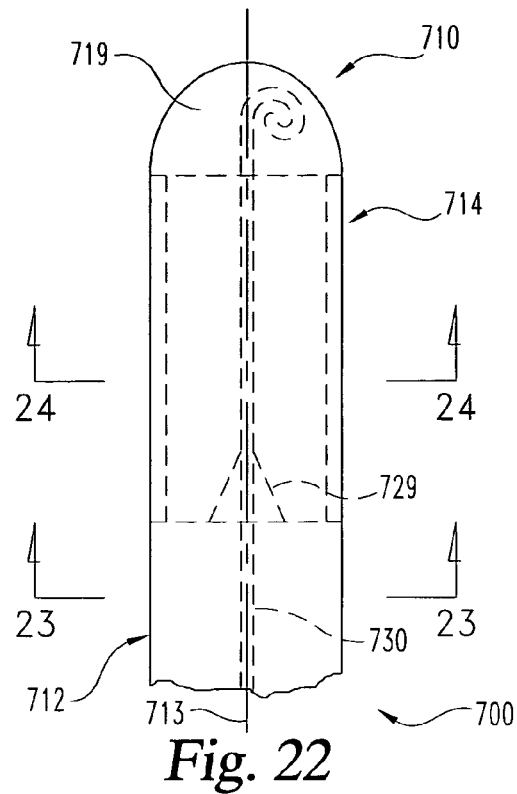
FIG. 22 is a plan view of a distal portion of another embodiment catheter with its ports in a closed condition.
Figure 23:
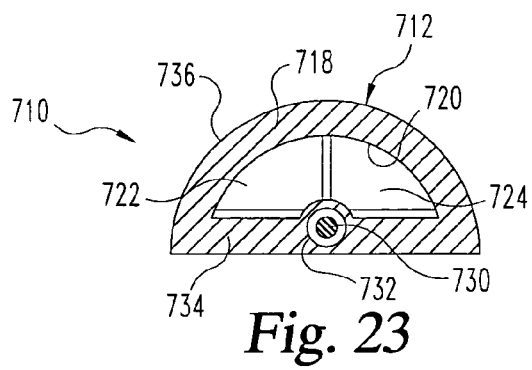
FIG. 23 is a section view along line 23-23 of FIG. 22.
Figure 24:
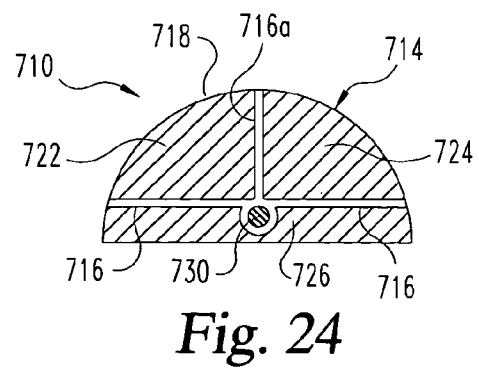
FIG. 24 is a section view along line 24-24 of FIG. 22.

Referring to FIGS. 22-24, there is shown a distal portion of one lumen part 710 of a catheter 700 including a body 712 and a distal portion 714. One or more ports 716 are provided along distal portion 714, and extend through wall 718 of body 712 in communication with a lumen 720. Distal portion 714 can be closed with an integral tip or cap 719 at its distal end to prevent fluid flow therethrough. In the illustrated embodiment, each port 716 is an elongated slit or gill that extends generally parallel to the longitudinal axis 713 of body 712. It should be understood that a second lumen part 710 of catheter 700 could be provided adjacent to lumen part 710 that is similar to lumen 710. Together, the lumen parts 710 provide separate flow paths for fluid ingress and fluid egress. Other embodiments contemplates that lumen 720 could be divided into separate, multiple lumens.

Three ports 716 are provided in wall 718 that extend radially through distal portion 714 approximately 90 degrees apart from the central port 716a. Other embodiments contemplate one or more ports 716, including two ports, four ports, or five or more ports. It is further contemplated that the ports can be evenly spaced or unevenly spaced about distal portion 714. Distal portion 714 can made with a material with sufficient flexibility so that the wall segments 722, 724, 726 between ports 716 can be flexed or deformed to open and close ports 716. In FIG. 22, distal portion 714 is in a first configuration or condition where ports 716 are closed. It is contemplated that in the closed condition wall 718 substantially seals ports 716 to prevent fluid flow from exiting or entering lumen 720 through ports 716. In FIG. 24, wall 18 has been manipulated to open one or more of the ports 716 to provide fluid communication between lumen 720 and an exterior of body 712 through the ports 716.

Manipulation of wall 718 can include displacing or deforming adjacent wall segments 722, 724, 726 along ports 716. In one embodiment, ports 716 are opened by deforming wall segments 722, 724, 726 along ports 716 to reduce the length of distal portion 714 from a first, undeformed length to a shorter, deformed length. One or more wall segments 722, 724, 726 along ports 716 can be expanded or separated from an adjacent wall segment 722, 724, 726 to open ports 716. The deformed portions of wall segments 722, 724, 726 can break loose any fibrous sheath formed about wall 718 adjacent to ports 716. Furthermore, deformation of wall segments 722, 724, 276 can provide ports 716 with sufficient size to accommodate any required blood flow through lumen 720. When ports 716 are closed, wall segments 722, 724, 726 along ports 716 abut one another along the entire length of each port 716 and with sufficient force to prevent fluid ingress and egress through ports 716 between lumen 720 and the vessel structure.

It is further contemplated that an actuating mechanism can be provided to facilitate opening and closing of ports 716, and maintain ports 716 in their opened and closed conditions. The actuating mechanism can include an actuator adjacent a proximal end portion of catheter 700 so that the actuator is positioned outside the body of the patient and readily accessible by the surgeon. The actuating mechanism can further include one or more actuating members 730 coupled to the actuator and extending along the catheter to a location adjacent to ports 716. One or more actuating members 730 are movable or operable with the actuator to manipulate wall segments 722, 724, 726 and open or close ports 716 as desired.

In FIGS. 22-24, actuating member 730 is positioned in a lumen 732 along a side wall 734 of body 712. Rounded wall 736 extends between opposite sides of side wall 734, and can include additional actuating members, but does not in the illustrated embodiment. Actuating member 730 can be in the form of a wire embedded in or surrounded by side wall 734, or that is positioned in a lumen formed in side wall 734. Such a lumen for receiving actuating member 730 could be formed by a flat wire coil of stainless steel or nitinol. Actuating member 730 can also be made from stainless steel, nitinol or any suitable material. Actuating member 730 extends through distal portion 714 between wall segments 722, 724 726 to distal cap 719. Actuating member 730 can be wrapped in cap 719 to prevent it from being pulled out of cap 719.

Ports 716 are positively closed by distally displacing actuating member 730 against cap 719, stretching distal portion 714 and forcing wall segments 722, 724, 726 into abutting engagement with one another. Since wall segments 722, 724, 726 occupy substantially all the cross-sectional area of distal portion 714, more surface area is provided along and between the adjacent wall segments 722, 724, 726 to form a positive seal than would be provided if lumen 720 were carried through distal portion 714 in the same size and shape as is provided in body 712. Ports 716 are opened by tensioning actuating member 730, compressing distal portion 714 between cap 719 and body 712. Other embodiments contemplate that the ports are normally closed by the material properties and configuration of wall segments 722, 724, 276 and open in response to fluid pressure, for example. Furthermore, wall segments 722, 724, 726 can include tapered portions 729 at the proximal ends thereof that taper inwardly toward ports 716 to facilitate fluid flow thereto from lumen 720 without abrupt changes in profile.

Figure 25:
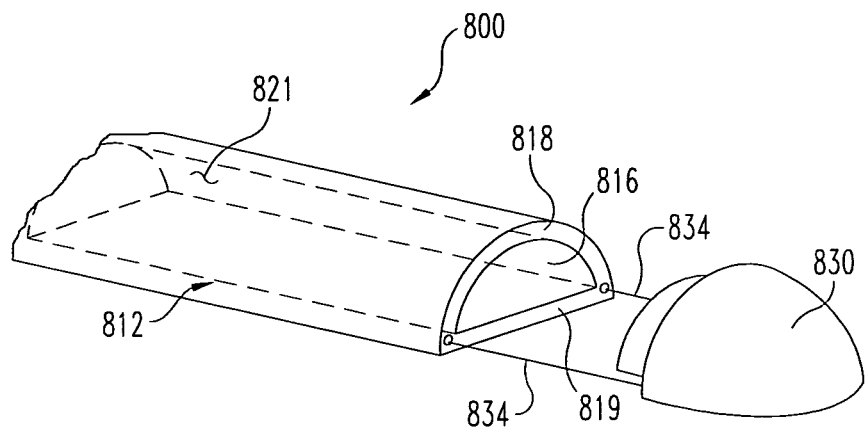
FIG. 25 is a perspective view of a portion of another embodiment catheter with its port in an open condition.
Figure 26:
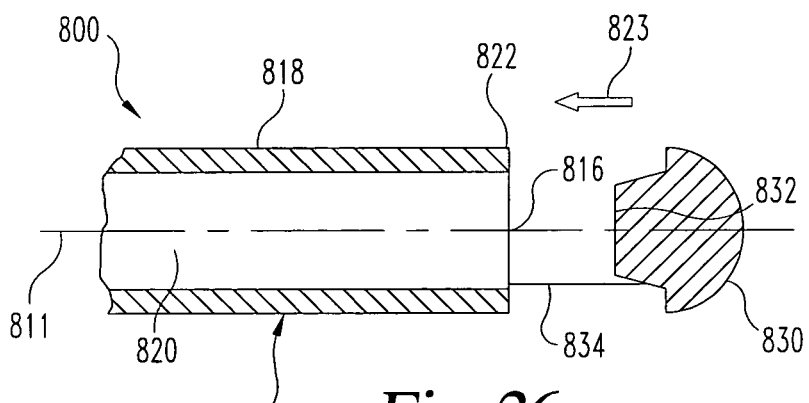
FIG. 26 is a section view of the catheter portion in FIG. 25.

In FIGS. 25-26 there is shown another embodiment catheter 800. Catheter 800 includes a lumen part 810 having a body 812 formed by a wall 818 extending about a lumen 820. Lumen 820 opens at a distal end of body 812 to form a port 816 for ingress and/or egress of fluid flow. It should be understood that catheter 800 can include one or more other lumen parts 810 that can provide additional lumens for fluid ingress or egress.

In addition, catheter 800 includes an end cap 830 associate with body 812 and movable relative thereto from an open position, as shown in FIG. 25, to a closed position. The port 816 can be opened by deforming catheter 800 from its closed position by displacing end cap 830 distally from its closed position to the open position. In the open position, cap 830 is spaced from distal end 822, resulting in a change of length of catheter 800, so that port 816 is open to permit fluid passage from or into lumen 820. End cap 830 is coupled to body 812 with one or more actuating members 834 that extend between body 812 and end cap 830. Actuating members 834 can be in the form of the form of a wire in wall 818 at or adjacent the junction of the linear portion 819 and the round, convex portion 821. Each actuating member 834 can be positioned in a lumen formed in wall 818. Such a lumen for receiving the respective actuating member 834 could be formed by a flat wire coil of stainless steel or nitinol. Actuating members 834 can also be made from stainless steel, nitinol or any suitable material. Actuating member 834 can be located at other locations about wall 818, and lumen part 810 can include one, two or three or more actuating members 834.

End cap 830 can be moved to the closed position from the open position by axially and proximally displacing end cap 830 toward port 816 along longitudinal axis 811 and into sealing engagement with body 812. Actuating members 834 can be coupled to an actuating mechanism to allow displacement of the actuating members 834, and thus end cap 830, proximally along axis 811 to the closed position. To open port 816, actuating members 834 are displaced distally with the actuator mechanism to displace cap 830 distally along axis 811 and relative to port 816 and body 812. End cap 830 can include a tapered proximal portion 832 that can facilitate receipt through port 816 into lumen 820. The tapered portion 832 can also allow cap 830 to self-center relative to port 816 and provide sealing engagement with wall 818.

Figure 27:
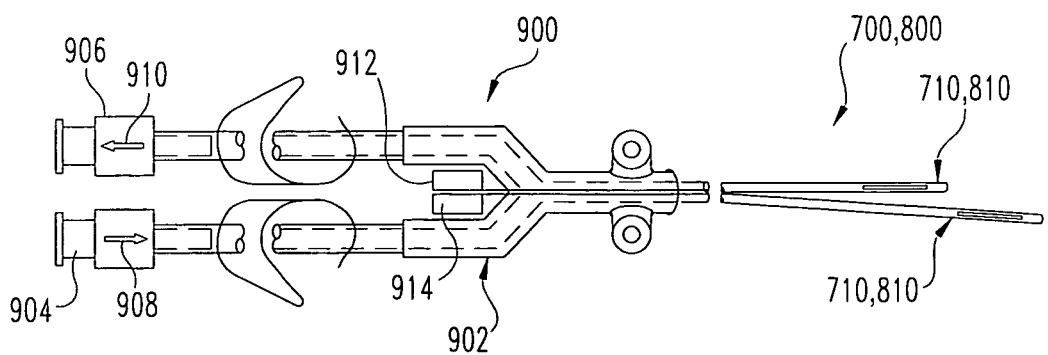
FIG. 27 is a plan view of a catheter assembly showing another embodiment actuating mechanism.

Referring now to FIG. 27, there is shown an example of an actuating mechanism 900 that can be employed with catheters 700, 800 or other catheter embodiments discussed herein. Catheters 700, 800 include lumen parts 710, 810 that are coupled together at a proximal hub 902. Proximal hub 902 can include a Y-shape that separates the two lumen parts for connection with fluid sources or other equipment at connectors 904, 906. In one embodiment, one of the lumen parts 710, 810 can be designated to provide fluid flow to the body of the patient and the other lumen part 710, 810 can be designated to receive fluid flow from the body of the patient, as indicated by arrow 908, 910.

The actuating members 730, 834 of the lumen parts 710, 810 can be coupled with an actuator adjacent hub 902. The actuator can include first and second slide buttons 912, 914. Each slide button is coupled to the one or more actuating members 730, 834 of the respective lumen part 710, 810.

Slide buttons 912, 914 allow movement of the actuating members of the respective lumen part 710, 810 along the wall of the lumen part. The separated slide buttons 912, 914 can be moved axially in either the proximal or distal direction, as desired, to effect corresponding independent and remotely activated movement of the distal portion 714 or end cap 830, depending on the lumen part 710, 180 employed with actuator mechanism 900. Such movement allows selective opening and closing of the one or more parts to allow fluid flow therethrough.

While the invention has been illustrated and described in detail in the drawings and foregoing description, the same is to be considered as illustrative and not restrictive in character. For example, for any embodiment catheter actuating mechanisms are contemplated that include micro-motors or other automatic or mechanical systems for opening and closing the fluid flow ports. All changes and modifications that come within the spirit of the invention are desired to be protected.

What is claimed is:

1. A dialysis catheter, comprising:
an elongate body extending between a distal end and a proximal end, said body including a first wall defining a first lumen for a fluid flow therethrough of at least 300 milliliters per minute out of a vasculature of a patient and a second wall defining a second lumen for a fluid flow therethrough of at least 300 milliliters per minute into the vasculature of the patient, wherein said body includes a first port and a second port at said distal end of said elongate body, said first port in communication with said first lumen and said second port in communication with said second lumen, and further comprising a first end cap and a second end cap at said distal end and an actuating mechanism at said proximal end, said first end cap being coupled to said actuating mechanism by at least both a first non-tubular wire, cable, rod, or bar that extends in said first wall along one side of said first lumen, the first non-tubular wire, cable, rod, or bar extending distally from a first actuator opening, and a second non-tubular wire, cable, rod, or bar that extends in said first wall along an opposite side of said first lumen, the second non-tubular wire, cable, rod, or bar extending distally from a second actuator opening, and said second end cap being coupled to said actuating mechanism by at least both a third non-tubular wire, cable, rod, or bar that extends in said second wall along one side of said second lumen, the third non-tubular wire, cable, rod, or bar extending distally from a third actuator opening, and a fourth non-tubular wire, cable, rod, or bar that extends in said second wall along an opposite side of said second lumen, the fourth non-tubular wire, cable, rod, or bar extending distally from a fourth actuator opening, wherein said actuating mechanism is operable to remotely move said first and second end caps away from said first port and said second port to an open condition and permit said fluid flows through each of said first port and said second port and said actuating mechanism is further operable to remotely move said first and second end caps toward said distal end to a closed condition in sealing engagement with said body to prevent said fluid flows through each of said ports, wherein the first, second, third, and fourth actuator openings are separate from the first port and the second port.

2. The catheter of claim 1, wherein said elongate body extends along a longitudinal axis and each of said first and second end caps is movable along said longitudinal axis between said open condition and said closed condition.

3. The catheter of claim 1, wherein said first end cap includes a first tapered proximal portion positionable through said first port into said first lumen when said first end cap is in the closed condition and said second end cap includes a second tapered proximal portion positionable through said second port into said second lumen when said second end cap is in the closed condition.

4. The catheter of claim 1, wherein said first non-tubular wire, cable, rod, or bar and said second non-tubular wire, cable, rod, or bar both extend along one side of said body and said third non-tubular wire, cable, rod, or bar and said fourth non-tubular wire, cable, rod, or bar both extend along an opposite side of said body.

5. The catheter of claim 4, wherein each of said first, second, third, and fourth non-tubular wires, cables, rods, or bars is coupled to a slide button of said actuating mechanism.

6. The catheter of claim 1, wherein said first lumen and said second lumen each define a D-shape.

7. The catheter of claim 1, wherein at least a portion of said first wall is integral with at least a portion of said second wall.

8. A dialysis catheter, comprising:
an elongate body defining a pair of lumens each configured to permit a fluid flow of at least 300 milliliters per minute therethrough, each of said lumens extending between a distal end and a proximal end, wherein each of said lumens includes a self-closing port at said distal end thereof in communication with a respective lumen of said lumens, and further comprising a pair of end caps at said distal ends of respective ones of said lumens and an actuating mechanism at said proximal ends of said lumens, each of said end caps being coupled to said actuating mechanism by at least two non-tubular wires, cables, rods, or bars that extend in a wall along a respective lumen of said lumens, wherein said actuating mechanism is operable to automatically move each of said end caps with said respective non-tubular wires, cables, rods, or bars away from said port of said respective lumen to an open condition and permit said fluid flow through said port of said respective lumen, and wherein said actuating mechanism is operable to automatically move each of said end caps toward said port of said respective lumen to a closed condition in sealing engagement with said body to prevent said fluid flow through said port of said respective lumen, and wherein each of said respective non-tubular wires, cables, rods, or bars extends distally through openings in a lateral surface of the elongate body.

9. The catheter of claim 8, wherein said actuating mechanism includes a pair of slide buttons each being associated with a respective one of said pair of lumens, each one of said pair of slide buttons being engaged to said respective at least two non-tubular wires, cables, rods, or bars and being operable to move said respective end cap between said open and closed conditions.

10. The catheter of claim 8, wherein said lumens are joined in a hub at said proximal ends of said lumens adjacent said actuating mechanism.

11. The catheter of claim 8, wherein said elongate body extends along a longitudinal axis and each of said end caps is movable along said longitudinal axis between said open condition and said closed condition.

12. The catheter of claim 8, wherein each of said end caps includes a tapered proximal portion positionable into said port of said respective lumen in said closed condition.

13. The catheter of claim 8, wherein
said pair of lumens includes a first lumen and a second lumen;
a first set of said at least two non-tubular wires, cables, rods, or bars comprises a first non-tubular wire, cable, rod, or bar that extends along one side of the first lumen and a second non-tubular wire, cable, rod, or bar that extends along an opposite side of the first lumen;
a second set of said at least two non-tubular wires, cables, rods, or bars comprises a third non-tubular wire, cable, rod, or bar that extends along one side of the second lumen and a fourth non-tubular wire, cable, rod, or bar that extends along an opposite side of said second lumen.

14. The catheter of claim 8, wherein each of said lumens and said wall of each of said lumens define a D-shape.

15. A catheter comprising:
an elongate body;
a first lumen extending within the elongate body to a first distal port;
a second lumen extending within the elongate body to a second distal port;
a first end cap coupled to a first actuating member and a second actuating member;
the first actuating member displaceably disposed within a wall of the elongate body and distally extending from a first actuator opening in a first distal lateral surface of the elongate body;
the second actuating member displaceably disposed within the wall of the elongate body and distally extending from a second actuator opening in the first distal lateral surface of the elongate body;
a second end cap coupled to a third actuating member and a fourth actuating member;
the third actuating member displaceably disposed within the wall of the elongate body and distally extending from a third actuator opening in a second distal lateral surface of the elongate body;
the fourth actuating member displaceably disposed within the wall of the elongate body and distally extending from a fourth actuator opening in the second distal lateral surface of the elongate body;
wherein the first, second, third, and fourth actuator openings are separate from the first and second distal ports.

16. The catheter of claim 15, wherein the first and second actuator openings and the first distal port are disposed in a first lateral plane along a longitudinal direction of the elongate body and the third and fourth actuator openings and the second port are disposed in a second lateral plane along the longitudinal direction of the elongate body.

* * * * *